United States Patent [19]
Pascarella et al.

[11] Patent Number: 5,484,443
[45] Date of Patent: Jan. 16, 1996

[54] INSTRUMENT FOR INSERTING A PROTECTIVE SLEEVE INTO THE MEDULLARY CANAL OF A BONE

[75] Inventors: Joanne M. Pascarella, Cordova, Tenn.; John V. Vanore, Burr Ridge, Ill.

[73] Assignee: Wright Medical Technology, Inc., Arlington, Tenn.

[21] Appl. No.: 310,651

[22] Filed: Sep. 22, 1994

Related U.S. Application Data

[63] Continuation of Ser. No. 37,510, Mar. 24, 1993, abandoned, which is a continuation of Ser. No. 817,265, Jan. 3, 1992, abandoned.

[51] Int. Cl.⁶ .............................. A61F 5/00; A61B 17/58
[52] U.S. Cl. .................................. 606/86; 606/99
[58] Field of Search ........................ 606/86, 87, 88, 606/89, 91, 99, 100; 623/22, 23

[56] References Cited

U.S. PATENT DOCUMENTS

| | | | |
|---|---|---|---|
| 2,187,852 | 1/1940 | Friddle | 606/100 |
| 3,036,482 | 5/1962 | Kenworthy | 606/100 |
| 3,334,624, | 8/1967 | Schneider | 606/100 |
| 3,626,935 | 12/1971 | Pollock | 606/100 |
| 4,305,394 | 12/1981 | Bertuch | 606/91 |
| 4,423,721 | 1/1984 | Otte | 606/100 |
| 4,462,395 | 7/1984 | Johnson | 606/100 |
| 4,621,630 | 11/1986 | Kenna | 606/89 |
| 4,878,918 | 11/1989 | Tari | 606/91 |
| 4,987,904 | 1/1991 | Wilson | 606/86 |
| 4,993,410 | 2/1991 | Kimsey | 606/100 |
| 4,994,064 | 2/1991 | Aboczky | 606/91 |
| 5,030,219 | 7/1991 | Matsen | 606/86 |
| 5,061,270 | 10/1991 | Aboczky | 606/99 |
| 5,061,271 | 10/1991 | Van Zile | 606/99 |
| 5,071,420 | 12/1991 | Paulos | 606/99 |

*Primary Examiner*—Michael A. Brown
*Attorney, Agent, or Firm*—Walker, McKenzie & Walker

[57] ABSTRACT

In accordance with the present invention, an instrument for surgically implanting a grommet for a flexible small bone joint replacement prostheses, such as a finger joint, is provided. The instrument includes a handle having a central axis with opposed proximal and distal ends, wherein the distal end of the handle is configured with a first connection portion. A head having opposed proximal and distal portions includes a base extending axially from the distal portion, the proximal portion of the head being configured with a second connection portion for releasable engagement with the first connection portion of the handle. A post protrudes distally from the base and includes a cross section which is tapered in a distal direction from a thicker portion at the intersection of the post with the base toward the tip of the post. The taper of the stem portion is adapted for mating with the grommet to be implanted into the medullary canal of bone.

21 Claims, 3 Drawing Sheets

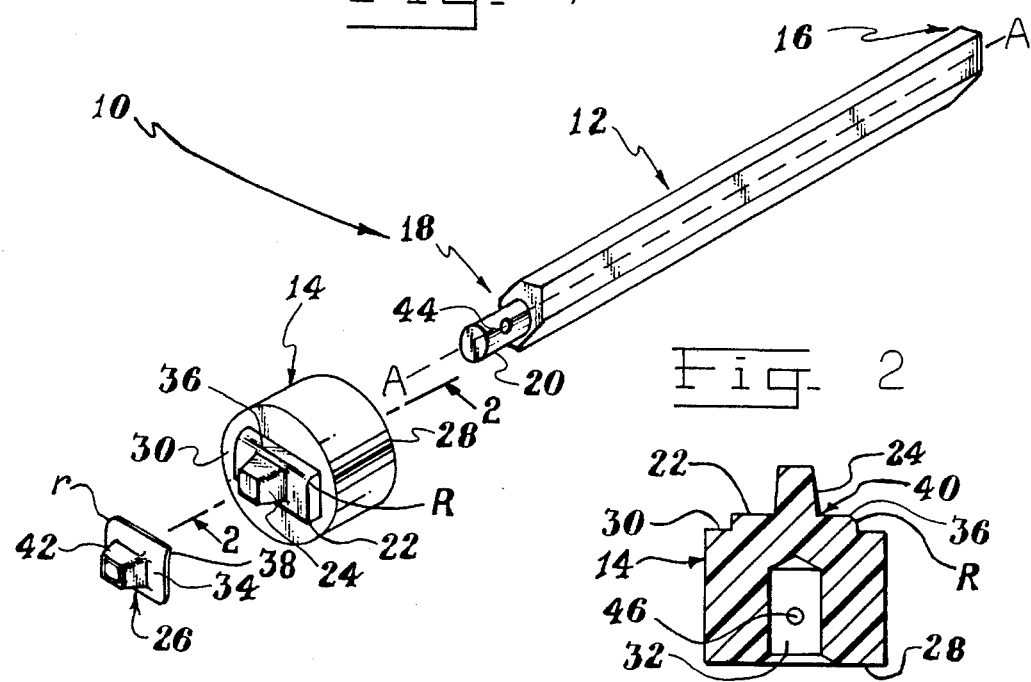

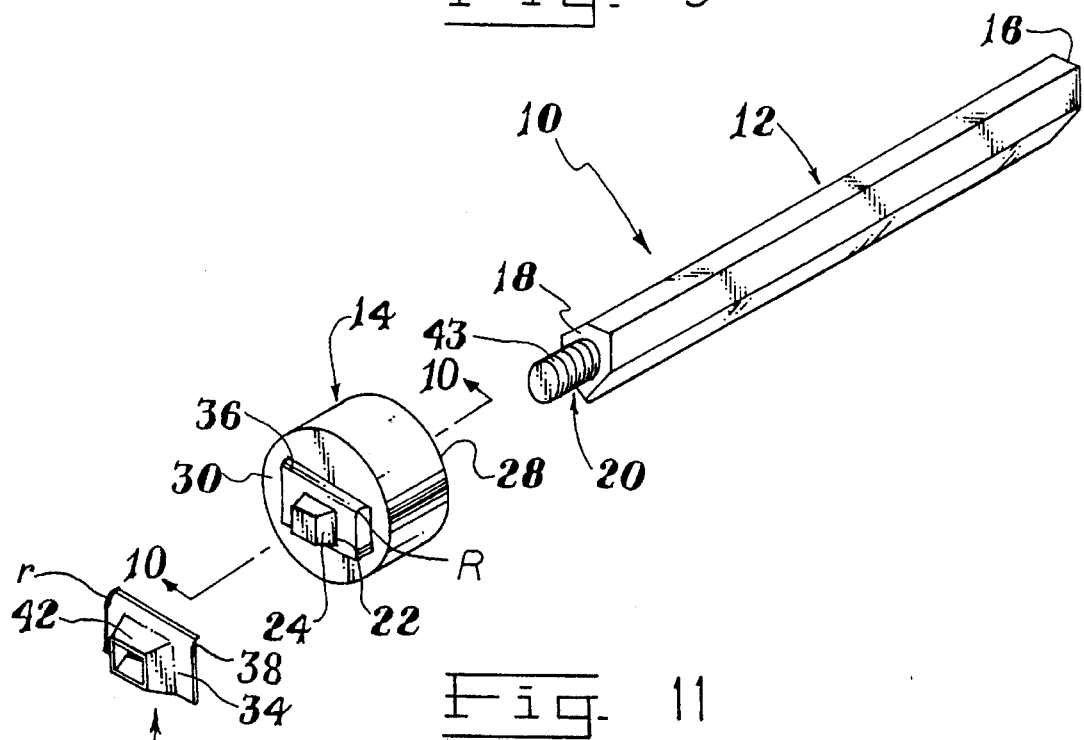
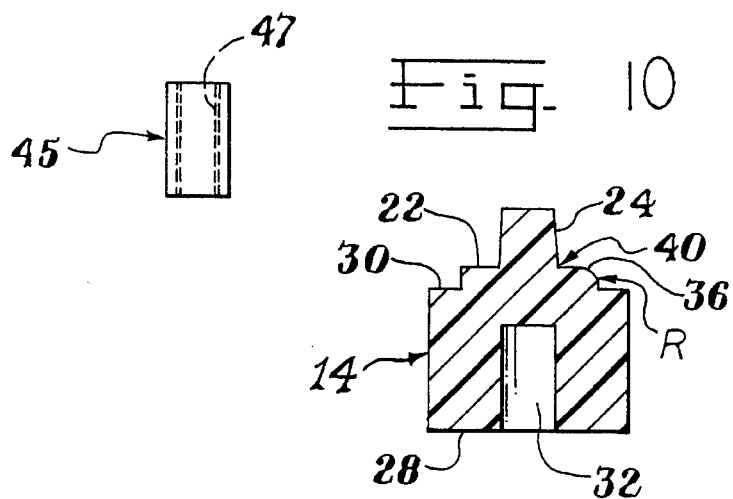

INSTRUMENT FOR INSERTING A PROTECTIVE SLEEVE INTO THE MEDULLARY CANAL OF A BONE

This is a continuation of application, application Ser. No. 08/037,510, filed Mar. 24, 1993, now abandoned, which is a continuation of now abandoned application, application Ser. No. 07/817,265, filed Jan. 3, 1992.

BACKGROUND OF THE INVENTION

1. Technical Field

This invention relates to surgical instrumentation for implanting a grommet for a bone joint replacement prosthesis, and more particularly an instrument for inserting a grommet into the medullary canal of a bone.

2. Description of the Prior Art

During surgical implantation of, for example, a toe or finger prostheses, it is typically necessary to utilize a grommet on the prostheses stems. Prostheses designed for use with grommet include a thickened mid-section and are fabricated from a flexible elastomeric, physiologically inert material, such as a cured silicone rubber, that is susceptible to lacerations and tearing at the stems which can lead to premature failure of the prostheses. The grommet shield the prostheses stems from shearing caused by sharp bone edges of the resected bone of the medullary canal believed to be responsible for lacerations and tearing.

The prostheses stems generally correspond to the dimension of the medullary canal of the bones adjacent the prostheses thickened midsection and are implantable within the canal. Prior to implantation of the stem, one grommet is surgically implanted within the medullary canal of the bone adjacent the thickened midsection before the stem is implanted into the medullary canal.

The above procedure requires an accurate press-fitting of the grommet into the medullary canal.

There remains a need for an instrument that can accurately insert the grommet into the medullary canal without bending, scratching, or distorting the grommet.

SUMMARY OF THE INVENTION

In accordance with the present invention, an instrument for surgically implanting a grommet for a flexible bone joint replacement prostheses is provided. The instrument comprises a handle having a central axis with opposed proximal and distal ends, wherein the distal end of the handle is configured with a first connection portion. A head having opposed proximal and distal portions, includes a base extending axially from the distal portion. The proximal portion of the head is configured with a second connection portion for mating engagement with the first connection portion of the handle. A post protrudes distally from the base and includes a cross-section which is tapered in a distal direction from a thicker portion at the intersection of the post with the base. The taper of the post is adapted for mating with the grommet to be press-fitted into the medullary canal of a bone. Means are provided for removably securing the head to the handle.

BRIEF DESCRIPTION OF THE DRAWINGS

The invention may be better appreciated by reference to the attached Drawings, which illustrate one or more preferred embodiments, wherein:

FIG. 1 is a perspective exploded isometric view of the instrument showing the handle, head, and a grommet to be inserted, according to the invention and showing the central axis A—A;

FIG. 2 is a cross sectional view of the head taken substantially along lines 2—2 of FIG. 1;

FIG. 3 is a perspective view showing the grommet of FIG. 1;

FIG. 4 is a perspective view showing a prostheses which is intended to cooperate with the grommet of FIG. 3;

FIG. 5 is a perspective view showing the prostheses of FIG. 4 with the protective grommet as they would be in place on the stem portions of the prostheses;

FIG. 6 is a perspective view showing the prostheses and grommets implanted in the medullary canals of adjoining bones of a finger joint;

FIG. 7 is a perspective view showing one stem portion of the prostheses implanted in the medullary canal of an adjoining bone of a joint, and a grommet press-fit into the medullary canal of the other adjoining bone;

FIG. 9 is a perspective exploded isometric view of the instrument showing the handle having a threaded portion, head, and a grommet to be inserted, according to the invention;

FIG. 10 is a cross-sectional view of the head taken substantially along lines 10—10 of FIG. 9; and FIG. 11 is a perspective view showing the insert that is to be press-fitted into the head of FIG. 10.

Figure 8:
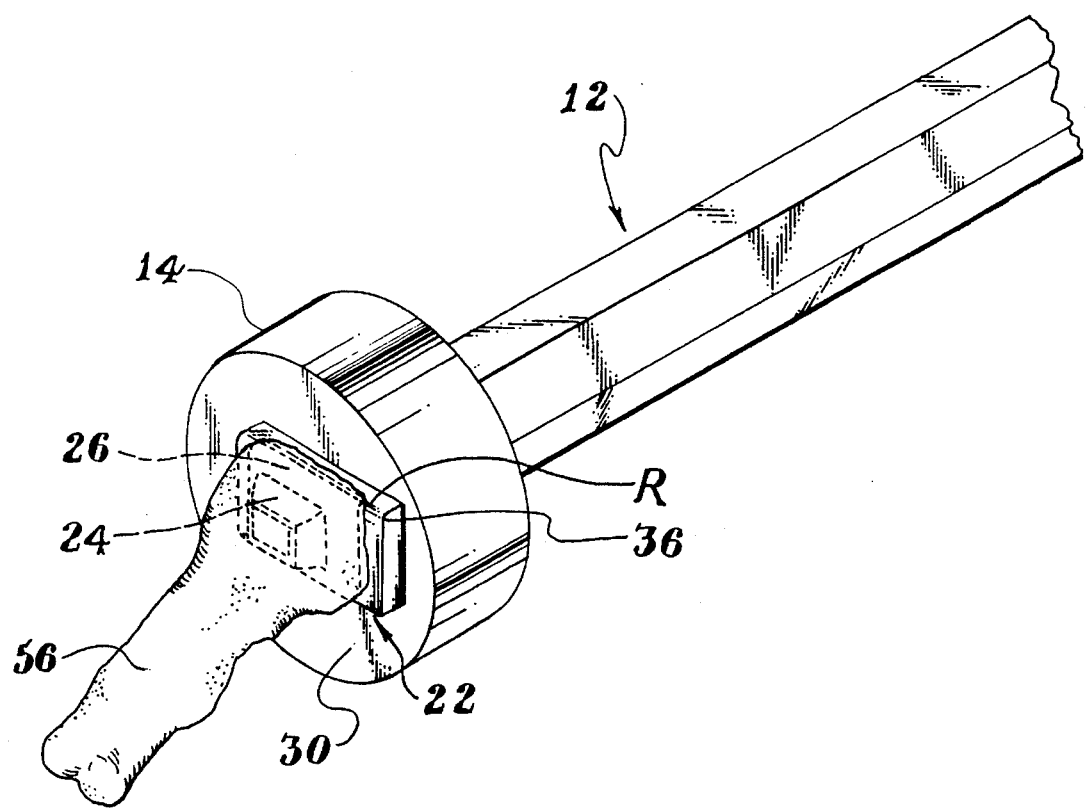
FIG. 8 is a perspective view showing a grommet being implanted into the medullary.

Further objects and advantages can be appreciated by reference to the ensuing Detailed Description, taken in conjunction with the abovementioned Drawings, wherein the reference numerals are used to designate corresponding structures of the Drawings.

DETAILED DESCRIPTION

Referring to FIG. 1, a preferred embodiment of an instrument for inserting a grommet, such as a grommet, is generally shown at 10. The instrument 10 comprises an elongated handle, generally indicated at 12, having a central axis, and a head which is indicated at 14. Handle 12, preferably made of stainless steel, further includes opposed proximal 16 and distal 18 ends, distal end 18 being configured with a first connection portion 20 for interconnecting the handle and head 14 with one another. The head 14 includes a base 22 with a protruding post 24 adapted for receiving grommet 26 to be implanted into the medullary canal. Means are further provided for removably securing head 14 to handle 12, as will be described in more detail below.

As shown in more detail with reference to FIGS. 1 and 2, head 14 has opposed proximal 28 and distal 30 portions, with base 22 extending axially from the distal portion. The proximal portion 28 is configured with a second connection portion 32 for mating with first connection portion 20 of handle 12, wherein head 14 and the handle are removably interconnected. Head 14 is formed from a high density TEFLON® or other material which is nonabrasive to a prostheses or grommet being implanted, and Is sized to be interchangeable, allowing a single handle to be used with different head sizes corresponding to different grommet sizes.

Referring In more detail to FIGS. 1–3, base 22 is generally rectangular in cross-section, corresponding to rectangular flanged section 34 of grommet 26, shown in FIG. 3. Base 22 supports grommet 26 and distributes the forces exerted during press-fitting of the grommet into the medullary canal 50, to flanged section 34, reducing the risk of bending the grommet. Base 22 further includes horizontal leading edge 36 having radius R adapted for mating with radius flanged section 38 also having a radius r, of implantable grommet 26.

Referring to FIGS. 2, 3 and 8, post 24 protrudes distally from base 22 and includes a cross-section tapered in a distal direction from a thicker portion 40 at the intersection of the post with the base. The tapered cross-section of post 24 is configured to mate with protrusion 42 of grommet 26 as the grommet is situated on the post for implantation. It should be understood that the length of post 24 is dependent on the size of the particular implant, and of sufficient length to hold grommet 26 on the post. Grommet 26 is of the type conventionally used in finger and toe joint replacement surgery. A further detailed description of the structure and use of the grommet may be found in U.S. Pat. No. 4,158,893 issued Jun. 26, 1979, and entitled: PROTECTIVE SLEEVE FOR IMPLANTABLE PROSTHESES AND METHOD OF PROTECTING THE PROSTHESIS, the entire disclosure of which is expressly incorporated by reference herein and relied upon.

Referring to FIGS. 9, 10, and 11, the means for securing head 14 to handle 12 preferably takes the form of thread portion 43 formed in first connection portion 20 of handle 12 which is threaded into second connection portion 32 via insert 45. Insert 45, preferably made of stainless steel, further having internal threads 47 is press-fitted into second connecting portion 32 to threadedly interconnect head 14 and handle 12. The structure for head 14 and grommet 16 are the same as FIGS. 1–3 with the exception of the above reference numbers.

Referring to FIGS. 1 and 2, in an alternate embodiment, the means for securing head 14 to handle 12 takes the form of ball plunger arrangement 44 formed in first connection portion 20 of handle 12, which is retained in a pilot hole 46 formed in head 14. First connection portion 20 including ball plunger arrangement 44 is inserted into second connection portion 32 formed in the proximal portion 28 of base 22. With the first connection portion 20 inserted in second connection portion 32, handle 12 is rotated until the ball plunger arrangement 44 engages pilot hole 46 to interconnect head 14 and the handle. Head 14 is easily disconnected from handle 12 by further rotating the handle until ball plunger arrangement 44 disengages pilot hole 46. A surgeon can quickly interchange different head sizes to correspond with different grommet sizes used during surgery while using the same handle.

The grommet 26 (FIG. 3), and prostheses 48, (FIGS. 4–7) are implanted into the prepared medullary canal 50 of bone 56 surgically as follows. The canal 50 is first drilled and reamed as shown in phantom in FIG. 6, the reaming corresponding to the dimensions of stems 52, 54 of prostheses 48. After prostheses 48 is implanted into the prepared canals 50, grommets 26 are situated over stems 52, 54 (FIGS. 5–7). Grommet 26 protects stems 52 and 54 from lacerations that may occur from sharp edges of bones adjacent the medullary canal 50. Lacerations of stems 52 and 54 are believed to be the starting point of tears, which could ultimately lead to premature joint failure.

Referring to FIG. 8, grommet 26 is shown situated on post 24 of base 22, and aligned with horizontal leading edge 36 of the base. With grommet 26 situated on post 24, the surgeon then press-fits the grommet into canal 50.

That which is claimed is:

1. An instrument for surgically implanting a grommet for a flexible bone joint replacement prostheses, comprising:

a handle having a central axis with opposed proximal and distal ends, the distal end being configured with a first connection comprising a threaded external surface;

a head connectable to said handle and having opposed proximal and distal portions, including a base extending axially from the distal portion, the proximal portion being configured with a second connection comprising a threaded internal bore for mating engagement with the first connection;

a post protruding distally from the base and having a cross-section which is tapered in a distal direction from a thicker portion at the intersection of the post with the base toward the tip of the post.

2. The instrument of claim 1 wherein the head is formed from a material which is nonabrasive to a prostheses or other component being implanted.

3. The instrument of claim 1 wherein the base has a generally rectangular cross section.

4. The instrument of claim 3 wherein the base includes a horizontal leading edge having a radius which is adapted for mating engagement with the implantable prostheses.

5. The instrument of claim 1 wherein the post has a generally rectangular cross section.

6. The instrument of claim 5 wherein the post is configured for mating with the protective grommet of the prostheses for allowing implantation of the prostheses.

7. An instrument for surgically implanting a grommet for a flexible finger or toe joint replacement prostheses, comprising:

a handle having a central axis with opposed proximal and distal ends, the distal end being configured with a first connection portion;

a head having opposed proximal and distal portions, including a base extending axially from the distal portion, and having a generally rectangular cross section, the proximal portion being configured with a second connection portion for mating engagement with the first connection portion, the base further includes a horizontal leading edge having a radius which is adapted for mating engagement with the implantable prostheses;

a post generally rectangular in cross section protruding distally from the base and having a cross section which is tapered in a distal direction from a thicker portion at the intersection of the post with the base toward the tip of the post; and means for removably securing the head to the handle.

8. An instrument for surgically implanting a grommet for a flexible finger or toe joint replacement prostheses, comprising:

a handle having a central axis with opposed proximal and distal ends, the distal end being configured with a first connection portion;

a head having opposed proximal and distal portions, including a base extending axially from the distal portion, and having a generally rectangular cross section, the proximal portion being configured with a second connection portion for mating engagement with the first connection portion, the base further includes a horizontal leading edge having a radius which is adapted for mating engagement with the implantable prostheses;

a post generally rectangular in cross section protruding distally from the base and having a cross section which is tapered in a distal direction from a thicker portion at the intersection of the post with the base toward the tip of the post; and means for removably securing the head to the handle.

9. An instrument for surgically implanting a grommet for a flexible bone joint replacement prostheses, comprising:

a handle having a central axis with opposed proximal and distal ends, the distal end being configured with a first connection comprising a plunger assembly containing a ball;

a head connectable to said handle and having opposed proximal and distal portions, including a base extending axially from the distal portion, the proximal portion being configured with a second connection comprising a pilot hole formed therein for mating engagement with the ball of the first connection, wherein the ball engages the pilot hole and locks the head to the handle;

a post protruding distally from the base and having a cross-section which is tapered in a distal direction from a thicker portion at the intersection of the post with the base toward the tip of the post.

10. An instrument for surgically implanting a grommet for a flexible bone joint replacement prostheses, comprising:

a handle having a central axis with opposed proximal and distal ends, the distal end being configured with a first connection comprising a threaded external surface;

a head connectable to said handle and having opposed proximal and distal portions, including a base extending axially from the distal portion, and having a generally rectangular cross-section, the proximal portion being configured with a second connection comprising a threaded internal bore for mating engagement with the first connection, the base further including a horizontal leading edge having a radius which is adapted for mating engagement with the grommet;

a post generally rectangular in cross-section protruding distally from the base and having a cross-section which is tapered in a distal direction from a thicker portion at the intersection of the post with the base toward the tip of the post.

11. An instrument for surgically implanting a grommet for a flexible finger replacement prostheses, comprising:

a handle having a central axis with opposed proximal and distal ends, the distal end being configured with a first connection comprising a threaded external surface;

a head connectable to said handle and having opposed proximal and distal portions, including a base extending axially from the distal portion, the proximal portion being configured with a second connection comprising a threaded internal bore for mating engagement with the first connection;

a post protruding distally from the base and having a cross-section which is tapered in a distal direction from a thicker portion at the intersection of the post with the base toward the tip of the post.

12. An instrument for surgically implanting a grommet for a flexible toe replacement prostheses, comprising:

a handle having a central axis with opposed proximal and distal ends, the distal end being configured with a first connection comprising a threaded external surface;

a head connectable to said handle and having opposed proximal and distal portions, including a base extending axially from the distal portion, the proximal portion being configured with a second connection comprising a threaded internal bore for mating engagement with the first connection;

a post protruding distally from the base and having a cross-section which is tapered in a distal direction from a thicker portion at the intersection of the post with the base toward the tip of the post.

13. An instrument for surgically implanting a grommet for a flexible finger joint replacement prostheses, comprising:

a handle having a central axis with opposed proximal and distal ends, the distal end being configured with a first connection comprising a plunger assembly containing a ball;

a head connectable to said handle and having opposed proximal and distal portions, including a base extending axially from the distal portion, the proximal portion being configured with a second connection comprising a pilot hole formed therein for mating engagement with the ball of the first connection, wherein the ball engages the pilot hole and locks the head to the handle;

a post protruding distally from the base and having a cross-section which is tapered in a distal direction from a thicker portion at the intersection of the post with the base toward the tip of the post.

14. An instrument for surgically implanting a grommet for a flexible toe joint replacement prostheses, comprising:

a handle having a central axis with opposed proximal and distal ends, the distal end being configured with a first connection comprising a plunger assembly containing a ball;

a head connectable to said handle and having opposed proximal and distal portions, including a base extending axially from the distal portion, the proximal portion being configured with a second connection comprising a pilot hole formed therein for mating engagement with the ball of the first connection, wherein the ball engages the pilot hole and locks the head to the handle;

a post protruding distally from the base and having a cross-section which is tapered in a distal direction from a thicker portion at the intersection of the post with the base toward the tip of the post.

15. An instrument for surgically implanting a grommet for a flexible bone joint replacement prostheses, comprising:

a handle having a central axis with opposed proximal and distal ends, the distal end being configured with a first connection portion; and a head connectable to said handle and having opposed proximal and distal portions, the proximal portion being configured with a second connection portion for mating engagement with the first connection portion;

the head including a base extending axially from the distal portion;

the head including a post protruding distally from the base and having a cross section which is tapered in a distal direction from a thicker portion at the intersection of the post with the base toward the tip of the post; the post having a truncated pyramidal shape.

16. The instrument of claim 15 in which said base has a generally rectangular cross section.

17. An instrument for surgically implanting a grommet for a flexible bone joint replacement prostheses, comprising:

a handle having a central axis with opposed proximal and distal ends, the distal end being configured with a first connection portion; and a head having opposed proximal and distal portions, the proximal portion being configured with a second connection portion for connection with the first connection portion;

the head including a base extending axially from the distal portion, the base having a generally rectangular cross section and including a horizontal leading edge having a radius which is adapted for mating engagement with the implantable prostheses;

the head including a post generally rectangular in cross section protruding distally from the base and having a cross section which is tapered in a distal direction from a thicker portion at the intersection of the post with the base toward the tip of the post; the having a truncated pyramidal shape.

18. An instrument for surgically implanting a grommet for a flexible bone joint replacement prostheses, comprising:

a handle having a proximal end and having a distal end; and a head having a proximal portion connected to the distal end of the base and having a distal portion;

the head including a base extending axially from the distal portion;

the head including a post protruding distally from the base for receiving the grommet;

the post having a truncated pyramidal shape tapered in a distal direction from a thicker portion at the intersection of the post with the base toward the tip of the post.

19. The instrument of claim 18 wherein the base has a generally rectangular cross section.

20. The instrument of claim 19 wherein the grommet includes a flanged section having a radius; and wherein the base includes a leading edge having a radius which is adapted for mating engagement with the radius of the flanged section of the grommet.

21. The instrument of claim 18 wherein the post has a generally rectangular cross section.

* * * * *